US00PP16324P2

(12) United States Plant Patent
Sakazaki

(10) Patent No.: US PP16,324 P2
(45) Date of Patent: Mar. 7, 2006

(54) *CALIBRACHOA* PLANT NAMED 'USCALI67'

(50) Latin Name: ***Calibrachoa* sp.**
Varietal Denomination: USCALI67

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 35 days.

(21) Appl. No.: 10/955,493

(22) Filed: Sep. 30, 2004

(51) Int. Cl.
*A01H 5/00* (2006.01)

(52) U.S. Cl. ..... Plt./263
(58) Field of Classification Search ..... Plt./263
See application file for complete search history.

(56) References Cited

U.S. PATENT DOCUMENTS

PP10,279 P * 3/1998 Murakami ..... Plt./356
PP12,086 P2 * 9/2001 Bessho et al. ..... Plt./263
PP12,486 P2 * 3/2002 Westhoff ..... Plt./263
PP12,508 P2 * 4/2002 Bessho et al. ..... Plt./263
PP14,028 P2 * 7/2003 Takeshita et al. ..... Plt./263
PP14,874 P2 * 6/2004 Sakazaki ..... Plt./263
PP15,448 P2 * 12/2004 Pierce ..... Plt./263
PP15,449 P2 * 12/2004 Pierce ..... Plt./263

OTHER PUBLICATIONS

UPOV ROM GTITM Computer Database, GTI Jouve Retrieval Software 2005/02 Citations for 'USCALI67'.*

* cited by examiner

*Primary Examiner*—Kent Bell
*Assistant Examiner*—W. C. Haas
(74) *Attorney, Agent, or Firm*—C. A. Whealy

(57) ABSTRACT

A distinct cultivar of *Calibrachoa* plant named 'USCALI67', characterized by its semi-upright to cascading plant habit; freely branching habit; freely flowering habit; relatively large light purple-colored flower; good weather tolerance; tolerant to rain and low and high temperatures; and resistance to *Thielaviopsis*.

1 Drawing Sheet

Botanical classification: *Calibrachoa* sp.
Cultivar designation: USCALI67.

BACKGROUND OF THE INVENTION

The present Invention relates to a new and distinct cultivar of *Calibrachoa* plant, botanically known as *Calibrachoa* sp., and hereinafter referred to by the cultivar name 'USCALI67 '.

The new *Calibrachoa* is a product of a planned breeding program conducted by the Inventor in Hikone, Shiga, Japan. The objective of the program is to create new heat-tolerant and disease-resistant *Calibrachoa* cultivars with semi-upright plant habit and attractive flower colors.

The new *Calibrachoa* originated from a cross-pollination made by the Inventor on Apr. 12, 2000 of a proprietary seedling selection of *Calibrachoa* identified as code number C501, not patented, as the female, or seed, parent with a proprietary seedling selection of *Calibrachoa* identified as code number C4601, not patented, as the male, or pollen, parent. The new *Calibrachoa* was selected by the Inventor on Jun. 24, 2001 in a controlled environment in Gensingen, Germany.

Asexual reproduction of the new cultivar by terminal cuttings taken in a controlled environment in Gensingen, Germany since Jun. 25, 2001, has shown that the unique features of this new *Calibrachoa* are stable and reproduced true to type in successive generations.

SUMMARY OF THE INVENTION

Plants of the cultivar USCALI67 have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'USCALI67'. These characteristics in combination distinguish 'USCALI67' as a new and distinct cultivar of *Calibrachoa:*

1. Semi-upright to cascading plant habit.
2. Freely branching habit.
3. Freely flowering habit.
4. Relatively large light purple-colored flowers.
5. Good weather tolerance; tolerant to rain and low and high temperatures.
6. Resistant to *Thielaviopsis.*

Plants of the new *Calibrachoa* differ primarily from plants of the parent selections primarily in flower color as plants of the female selection have darker purple-colored flowers and plants of the male parent have white-colored flowers.

Plants of the new *Calibrachoa* can be compared to plants of the cultivar Colorburst Pink, not patented. In side-by-side comparisons conducted in Gensingen, Germany, plants of the new *Calibrachoa* had a more upright plant habit and larger flowers than plants of the cultivar Colorburst Pink.

Plants of the new *Calibrachoa* can be compared to plants of the cultivar Sunbelkubu, U.S. Plant Pat. No. 10,279. In side-by-side comparisons conducted in Gensingen, Germany, plants of the new *Calibrachoa* had a more upright plant habit and larger flowers than plants of the cultivar Sunbelkubu.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Calibrachoa*.

The photograph at the top of the sheet is a close-up view of typical flowers and leaves of 'USCALI67'.

The photograph at the bottom of the sheet comprises a side perspective view of a typical plant of 'USCALI67' grown in a container.

DETAILED BOTANICAL DESCRIPTION

In the following description, color references are made to The Royal Horticultural Society Colour Chart, 1995 Edition, except where general terms of ordinary dictionary significance are used. Plants grown in 12.5 -cm containers were used for the aforementioned photographs and following description. Plants were about seven weeks from planting rooted cuttings. Plants were grown under conditions which closely approximate commerical production conditions during the spring in Bonsall, Calif. in an outdoor nursery. During the production period, day temperatures ranged from 18° C. to 35° C. and night temperatures ranged from 10° C. to 24° C.

Botanical classification: *Calibrachoa* sp. cultivar USCALI67.

Parentage:

*Female, or seed, parent.*—Proprietary seedling selection of *Calibrachoa* sp. identified as code number C501, not patented.

*Male, or pollen, parent.*—Proprietary seedling selection of *Calibrachoa* sp. identified as code number C4601, not patented.

Propagation:

*Type cutting.*—Terminal vegetative cuttings.

*Time to initiate and develop roots.*—Summer: About three weeks at 20° C. Winter: About four weeks at 20° C.

*Root description.*—Fine, freely-branching; whitish in color.

Plant description:

*Form.*—Annual flowering plant; initially upright to semi-upright, eventually cascading; uniformly mounded appearance.

*Usage.*—Appropriate for hanging basket, window boxes and patio containers.

*Plant height (from soil level to top of plant plane).*—About 10 cm.

*Plant diameter.*—About 45 cm.

*Growth rate.*—Moderate growth rate; vigorous.

*Branching habit.*—Freely branching, about five primary branches per plant each with multiple secondary and tertiary branches; pinching is typically not required.

*Lateral branch description.*—Length: About 30 cm. Diameter: About 2 mm. Internode length: About 1.2 cm. Texture: Pubescent. Color: 144A.

*Foliage description.*—Arrangement: Alternate until flowering, then opposite; simple. Length: About 2.8 cm. Width: About 1.2 cm. Shape: Elliptic. Apex: Broadly acute. Base: Attenuate. Margin: Entire. Texture, upper surface: Slightly pubescent. Texture, lower surface: Slightly glandular; pubescent. Venation pattern: Pinnate; arcuate. Color: Developing foliage, upper and lower surfaces: 146B. Fully expanded foliage, upper surface: 146A. Fully expanded foliage, lower surface: 146B. Venation, upper surface: 146C. Venation, lower surface: 146B. Petiole: Length: About 1 cm. Diameter: About 1.5 mm. Texture, upper and lower surfaces: Smooth. Color, upper surface: 144B. Color, lower surface: 144C.

Flower description:

*Flower type and habit.*—Flowers face upright or outward; single, relatively large, axillary; salverform. Flowers persistent. Freely flowering habit, about 65 flowers per lateral stem. Flowers not fragrant. Flowers face outward and bending upwardly.

*Natural flowering season.*—April to September in Southern California; flowering continuous during this period.

*Time to flower.*—Early flowering; plants begin flowering about four to six weeks after planting.

*Flower longevity on the plant.*—About three to five days.

*Flower size.*—Diameter: About 2.6 cm by 2.8 cm. Depth: About 2.4 cm. Tube length: About 1.7 cm. Flower throat diameter: About 7 mm by 9 mm. Flower tube diameter: About 2 mm.

*Flower buds.*—Length: About 2 cm. Diameter: About 6 mm. Shape: Roughly oblong, slender. Color: 75B.

*Corolla.*—Arrangement/appearance: Single whorl of five petals, fused into flared trumpet. Petal length from throat: About 1.1 cm. Petal width: About 1.3 cm. Petal shape: Roughly fan-shaped. Petal apex: Obtuse with central point. Petal margin: Entire. Petal texture, upper and lower surfaces: Smooth, glabrous; satiny. Throat texture: Smooth. Tube texture: Slightly pubescent. Color: Petal, when opening, upper surface: 75C. Petal, when opening, lower surface: 75D. Petal, opened flower, upper surface: 75B; towards the throat, 82A; at the throat, 85A; venation, 77B; flower color becoming closer to 75C to 75D with development. Petal, opened flower, lower surface: 77C; towards the margins, 75D; venation, 77C to 77D. Flower throat (inside): 8A to 8B; venation, 146D. Flower tube (outside): Ground color, 10D; appears airbrushed with 77B to 77C; venation, 77A.

*Sepals.*—Arrangement/appearance: Single whorl of five sepals, fused at base; star-shaped. Length: About 1 cm. Width: About 3 mm. Shape: Narrowly elliptic. Apex: Acute. Margin: Entire. Texture, upper and lower sufaces: Slightly glandular; pubescent. Color, upper and lower surfaces: 144A.

*Peduncles.*—Length: About 1.5 cm. Width: About 1 mm. Strength: Moderately strong. Angle: About 30° C. to 45° from vertical. Texture: Slightly pubescent. Color: 144B.

*Reproductive organs.*—Stamens: Quantity: Five per flower. Anther shape: Oval. Anther length: Less than 1 mm. Anther color: 11A. Pollen amount: Scarce. Pollen color: 13B. Pistils: Quantity: One per flower. Pistil length: About 8 mm. Stigma shape: Oval. Stigma color: 144A. Style length: About 5 mm. Style color: 145D. Ovary color: 144B.

*Seed/fruit.*—Seed and fruit production has not been observed.

Disease/pest resistance: Plants of the new *Calibrachoa* have been noted to be resistant to *Thielavopsis*. Plants of the new *Calibrachoa* have not been noted to be resistant to other pathogens and pests common to *Calibrachoas*.

Weather/temperature tolerance: Plants of the new *Calibrachoa* are tolerant to rain and wind and have been observed to tolerate temperatures from 1° C. to 41° C.

It is claimed:

1. A new and distinct cultivar of *Calibrachoa* plant named 'USCALI67', as illustrated and described.

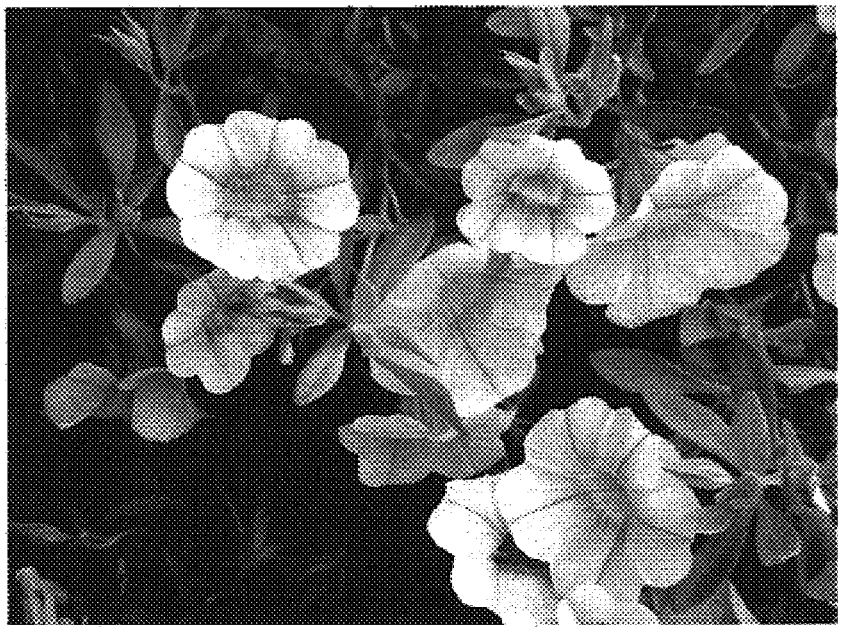
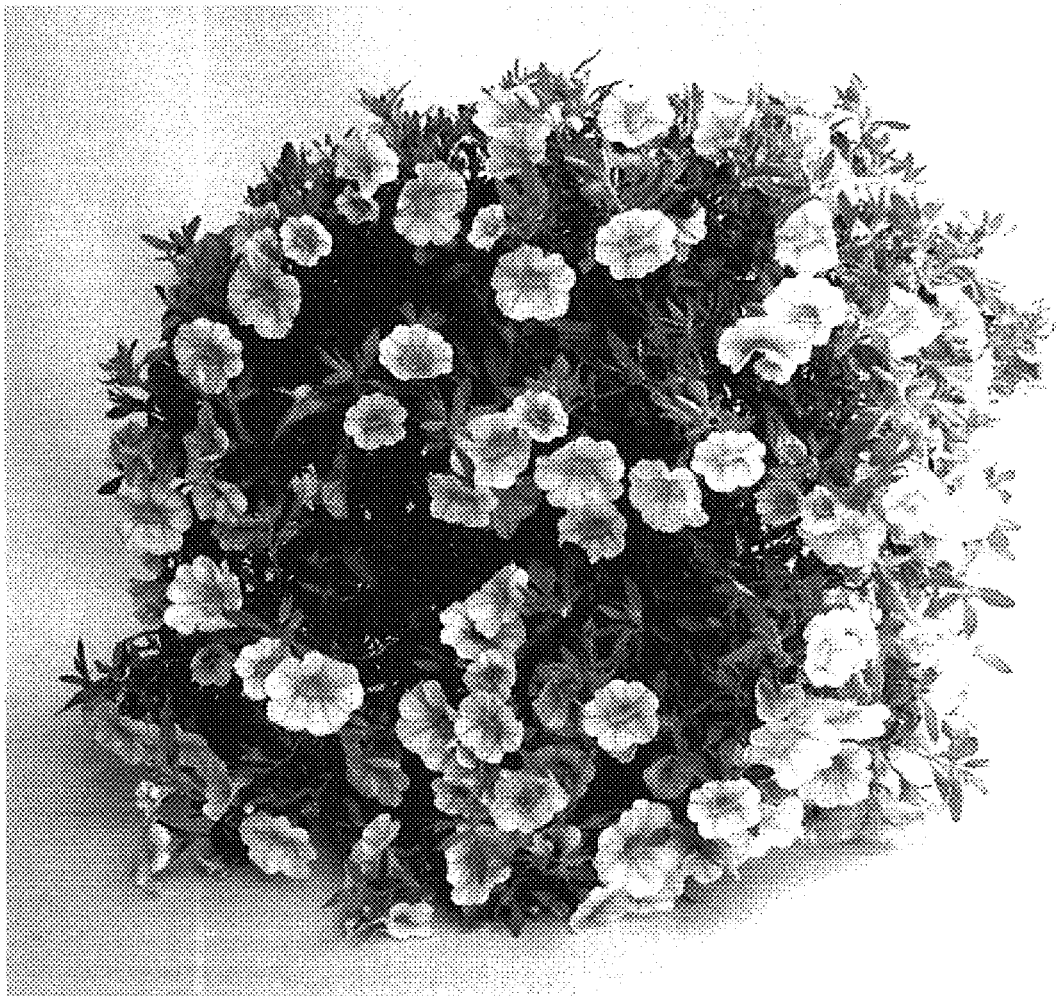

* * * * *